United States Patent
Wakui et al.

(10) Patent No.: US 7,531,706 B2
(45) Date of Patent: May 12, 2009

(54) PROCESS FOR PRODUCING OLEFIN BY CATALYTIC CRACKING OF HYDROCARBON

(75) Inventors: Kenichi Wakui, Chiba (JP); Yoshihiro Nakamura, Chiba (JP); Mitsuaki Hayashi, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 509 days.

(21) Appl. No.: 10/532,097

(22) PCT Filed: Oct. 21, 2003

(86) PCT No.: PCT/JP03/13425

§ 371 (c)(1), (2), (4) Date: Nov. 9, 2005

(87) PCT Pub. No.: WO2004/037951

PCT Pub. Date: May 6, 2004

(65) Prior Publication Data

US 2006/0116544 A1     Jun. 1, 2006

(30) Foreign Application Priority Data

Oct. 28, 2002   (JP) .............................. 2002-312539

(51) Int. Cl.
*C07C 4/06* (2006.01)
*C10C 11/05* (2006.01)
*B01J 29/06* (2006.01)

(52) U.S. Cl. ..................... 585/651; 585/652; 585/653; 208/114; 208/120.05; 208/120.1; 208/121; 208/122; 502/65; 502/71; 502/73; 502/77

(58) Field of Classification Search ......... 585/651–653; 208/114, 120.05, 120.1, 121, 122; 502/65, 502/71, 73, 77

See application file for complete search history.

(56) References Cited

U.S. PATENT DOCUMENTS

| 3,542,897 A | 11/1970 | Wattimena |
| 4,111,793 A | 9/1978 | Kolombos et al. |
| 4,956,075 A | 9/1990 | Angevine et al. |

FOREIGN PATENT DOCUMENTS

| EP | 210599 | 2/1987 |
| EP | 211340 | 2/1987 |
| EP | 211341 | 2/1987 |
| EP | 395345 | 10/1990 |
| EP | 925831 | 6/1999 |
| JP | 9-324182 | 12/1997 |
| WO | 96/34930 | 11/1996 |
| WO | WO 00/31215 | * 6/2000 |

* cited by examiner

*Primary Examiner*—In Suk Bullock
(74) *Attorney, Agent, or Firm*—Oblon, Spivak, McClelland, Maier & Neustadt, P.C.

(57) ABSTRACT

A process for producing olefin by catalytic cracking of hydrocarbon material characterized in employing zeolite of pentasil type comprising rare earth elements and at least one of manganese or zirconium as a catalyst. It enables to produce light olefin such as ethylene, propylene, and so on with selectively high yield and with long term stability, by catalytic cracking of gaseous or liquid hydrocarbon as ingredients under lower temperature than the conventional method and suppressing by-product such as aromatic hydrocarbon or heavy substances.

13 Claims, No Drawings

PROCESS FOR PRODUCING OLEFIN BY CATALYTIC CRACKING OF HYDROCARBON

TECHNICAL FIELD

The present invention relates to a process for producing olefin by catalytic cracking of hydrocarbon. More particularly, the present invention relates to a process for producing light olefin, mainly ethylene and propylene by catalytic cracking of hydrocarbon material with the use of a specific catalyst.

BACKGROUND ART

Light olefins such as ethylene, propylene and so on are substances that are important as raw materials of various chemicals. Conventionally, decomposition by heating among an external heat-type tubular furnace and under the atmosphere of steam with the use of materials of gaseous hydrocarbon such as ethane, propane, butane and so on or of liquid hydrocarbon such as naphtha and so on is adopted broadly as a process for producing light olefin. However, the decomposition by heating has economic disadvantages such that it requires an elevated temperature of 800° C. or higher in order to raise olefin yield, and accordingly, that it must employ expensive materials for the apparatus.

Therefore, a catalytic cracking method of hydrocarbons with the use of catalyst has been discussed in various ways. Among these, many examples are reported about the cases of employing solid acids, particularly penta-sil type zeolite such as ZSM-5, because it is advantageous in achieving relatively high ethylene yield and propylene yield (about 10 to 30% by mass respectively) at a reaction temperature of around 500 to 700° C.

For example, catalytic cracking methods employing ZSM-5 type catalyst having specific acidity and acid strength (refer to, for example, Japanese Unexamined Patent Application Laid-Open Nos. Hei 3-504737 and Hei 6-346062), and employing ZSM-5 type catalyst containing transition metals such as copper, cobalt and so on (refer to, for example, Japanese Unexamined Patent Application Laid-Open Nos. Hei 2-1413 and Hei 2-184638) are disclosed. Further, catalytic cracking methods employing ZSM-5 type catalyst containing rare earth element (refer to, for example, U.S. Pat. Nos. 5,232,675 and 5,380,690, European Patent No. 727404, Japanese Unexamined Patent Application Laid-Open Nos. Hei 11-180902 and Hei 11-253807) are disclosed. Problems are generally reported that carbon (coke) generated by excessive decomposition of hydrocarbons or hydrogen migration reaction adheres on the catalyst in reaction employing these zeolite catalyst, and causes loss of catalyst activity. Accordingly, continuous recovery by fluidized bed system reaction (refer to, for example, U.S. Pat. Nos. 5,232,675 and 5,380,690 and European Patent No. 727404) or reaction under the coexistence of steam in large amount (refer to, for example, Japanese Unexamined Patent Application Laid-Open Nos. Hei 11-180902 and Hei 11-253807) becomes necessary. However, there are problems that dealumination from zeolite lattice is caused by high-temperature steam being generated with combustion of steam or carbon introduced for the purpose of recovery, thereby induces permanent loss of catalyst activity. Therefore, improvement in hydrothermal stability of zeolite is unavoidable for using these zeolite catalysts industrially for a long time.

Hydrothermal stability of zeolite generally improves depending on an improvement of its crystallinity or on an augmentation of $SiO_2/Al_2O_3$ ratio. For example, a high silica type zeolite with $SiO_2/Al_2O_3$ mole ratio of 10 or more is reported as superior in heat resistance (refer to "Studies in surface Science and Catalysis", 1996, volume 105, p. 1549). However, these catalysts lack sufficient durability in application for a long period under industrial conditions, and therefore, various kinds of improvement are researched.

For example, ZSM-5 type zeolite of high hydrothermal stability containing transition metals such as Fe, Cu, Co, Ni, Cr, Mn, etc. and potassium or cesium (refer to, for example, Japanese Unexamined Patent Application Laid-Open Nos. Hei 4-50115, Hei 4-55310, Hei 4-78443 and Hei 4-78444) is not employable as a cracking catalyst because it contains alkali metal such as potassium, cesium, etc., and because acid strength is poor. Although there is a paper describing that ZSM-5 type catalyst containing Mn improves hydrothermal stability, catalytic property in catalytic cracking is indistinct (refer to "Studies in surface Science and Catalysis", 1996, volume 105, p. 1549). Further, although Japanese Unexamined Patent Application Laid-Open No. Hei 8-299166 discloses catalytic cracking reaction of hydrocarbon with the use of ZSM-5 type catalyst containing Mn and/or Re, there is no description about durability, and olefin selectivity is so small as 40% or lower because there are much aromatic by-product.

Furthermore, although fluid catalytic cracking methods with the use of catalyst consisting of zeolite and Mn dispersed in inorganic matrix are disclosed, they are aiming production of gasoline and reporting that containing Mn among zeolite is not preferable because octane value of gasoline decreases (refer to Japanese Unexamined Patent Application Laid-Open Nos. Hei 8-299166 and Hei 11-300210). Moreover, although U.S. Pat. No. 4,956,075 discloses that gasoline with high octane value is obtained by catalytic cracking method with the use of large pore size (Y type) zeolite modified with Mn and rare earth element, not only ethylene and propylene are almost not obtained but also there is no description about durability.

Improvement in hydrothermal stability of zeolite by other modifier such as, for example, Zr or so is disclosed, however, it is discussed about under relatively low temperature of around 400° C., and it is not clear about combined effect with rare earth element or about whether it can be applied effectively in producing olefin or not (refer to, for example, Japanese Unexamined Patent Application Laid-Open No. Hei 3-505844).

As the foregoing description, any catalytic cracking method in which catalytic cracking of hydrocarbon contributes for producing olefin with high yield and stably for a long term is not established yet.

DISCLOSURE OF THE INVENTION

The object of the present invention is to provide a process for producing olefin by catalytic cracking of the hydrocarbon which enables to produce light olefin such as ethylene, propylene, and so on with selectively high yield and with long term stability, by catalytic cracking of gaseous or liquid hydrocarbon as materials under lower temperature than the conventional method and suppressing by-product such as aromatic hydrocarbon or heavy substances.

As the result of intensive researches and studies to achieve the above object by the present inventors, it was found that penta-sil type zeolite containing rare earth element and manganese and/or zirconium improves hydrothermal stability and that olefin is obtained by catalytic cracking reaction of hydrocarbon with high yield and with a long term stability, resulting in completion of the present invention.

Namely, the present invention provides:
(1) A process for producing olefin by catalytic cracking of hydrocarbon material characterized in employing penta-sil type zeolite comprising rare earth elements and at least one of manganese or zirconium as a catalyst;
(2) The process for producing olefin according to the above item (1), wherein the contents of the rare earth elements in the catalyst falls within the range of from 0.4 to 20 expressed as atomic ratio of aluminum in zeolite;
(3) The process for producing olefin according to the above item (1), wherein the total contents of manganese and zirconium in said catalyst falls within the range of from 0.1 to 20 expressed as mole ratio of aluminum in zeolite;
(4) The process for producing olefin according to the above item (1), wherein said catalyst further comprises phosphorous in an amount of from 0.1 to 5% by mole;
(5) The process for producing olefin according to the above item (1), wherein the mole ratio of $SiO_2/Al_2O_3$ among zeolite in said catalyst is from 25 to 800; and
(6) The process for producing olefin according to the above item (1), wherein a catalytic reaction is carried out under the presence of steam.

THE PREFERRED EMBODIMENT TO CARRY OUT THE INVENTION

Gaseous or liquid hydrocarbons at ordinary temperature and under ordinary pressure are usable as hydrocarbon materials employed in the present invention. Paraffin having 2 to 30 carbon atoms, preferably 2 to 20 carbon atoms or hydrocarbon materials comprising the paraffin as the main component (at least 10% by mass) is generally used. Typical examples of the hydrocarbon materials include paraffin such as ethane, propane, butane, pentane, hexane, etc., or light hydrocarbon fractions such as naphtha, light oil, etc. Further, the material component is not limited to saturated hydrocarbons but expanded to the compounds containing a component having unsaturated bond.

The catalyst of the present invention essentially consists of penta-sil type zeolite containing rare earth element and containing manganese and/or zirconium. ZSM-5 and/or ZSM-11 is particularly preferable as the zeolite. $SiO_2/Al_2O_3$ mole ratio of the zeolite is from 25 to 800, preferably from 40 to 600, and more preferably from 80 to 300.

Although any kind of the rare earth element may be employable, preferable examples of the rare earth element include lanthanum, cerium, praseodymium, neodymium, samarium, gadolinium, dysprosium, etc. Each rare earth element may be employed alone or in combination of two or more kinds thereof. Modification of rare earths to catalyst employs various kinds of salt, for example, acetate, nitrate, halide, sulfate, carbonate or alkoxide, acetylacetonato and so on, by means of an ion exchange method, an impregnation method, a hydrothermal crystallization method or other method.

Either one kind or both of manganese and zirconium must be essentially contained in the catalyst additionally to the rare earth element in order to reveal the property of the main catalyst. The introduction of manganese and/or zirconium to the zeolite may be carried out by an ion exchange method, an impregnation method, a hydrothermal crystallization method or other method each with the use of various chemical compounds thereof respectively. The order of modifying rare earths, manganese and zirconium to zeolite is not particularly specified; however, modifying rare earth element after the modification of manganese and/or zirconium may be preferable.

It is important that the rare earth element, manganese and/or zirconium are supported on or contained in the zeolite in the main catalyst, and merely combining the zeolite with rare earths, manganese and/or zirconium compound (oxides, etc.) physically does not exhibit the effect of the main catalyst.

Among the catalyst of the present invention, the content of rare earth element is 0.4 to 20, preferably 0.6 to 5, and more preferably 1 to 3 expressed with atomic ratio to aluminum in zeolite. When the content is smaller than 0.4, by-product such as heavy coke or aromatic compound increases, and when the content exceeds 20, catalytic activity loses and olefin yield falls down. The content of manganese and/or zirconium expressed as a ratio of the total mol number to the mol number of aluminum in zeolite is from 0.1 to 20, preferably from 0.5 to 10, and more preferably from 1 to 5. When the content is smaller than the above value, hydrothermal stability degrades, and when it is too great, the catalytic activity loses. The effect of both the rare earth element and manganese and/or zirconium seem to enhance durability of catalyst and to suppress generation of by-product because modification by only manganese and/or zirconium without rare earth element degrades hydrothermal stability and increase the by-product.

Configuration of the catalyst in the present invention may be any of powdery, molding products, etc., without being particularly specified. Further, these catalysts may contain other components than zeolite, rare earth element, manganese and/or zirconium such as, for example, alkali elements, alkaline earth elements, transition metals, noble metals, halogens, phosphors, binders, etc. The catalysts may be used by combining with fillers such as silica, alumina, magnesia or quartz sands, etc.

With regards to the style of the catalytic cracking reaction in the present invention is not particularly specified, however, the catalytic cracking reaction may be carried out by supplying hydrocarbon materials to the catalytic layer wherein the catalyst is filled employing a style of reactor such as fixed bed, moving bed, fluidized bed, etc. In this occasion, the hydrocarbon materials may be diluted with nitrogen, hydrogen, helium, steam or so.

The reaction temperature falls within the range of from 350 to 780° C., preferably from 500 to 750° C., and more preferably from 600 to 700° C. Although the catalytic cracking reaction may be carried out even under the temperature of exceeding 780° C., generation of methane and coke will increase abruptly. Further, when the temperature is lower than 350° C., the yield of olefin per passage will decrease because enough activity will not be provided.

The reaction pressure may be effective with ordinary pressure, reduced pressure or compressed pressure, however, ordinary pressure or a little compressed pressure may be usually adopted.

Carrying out the present invention under the foregoing condition enables to efficiently decompose the hydrocarbon materials under low temperature thereby to produce light olefins such as ethylene, propylene and so on with high yield.

The present invention shall be explained below in further details with reference to examples, but the present invention shall by no means be restricted by the following examples.

EXAMPLES

Example 1

A powdery proton type ZSM-5 zeolite in an amount of 4 g as the zeolite was impregnated into an aqueous solution (prepared by dissolving 0.62 g of $MnSO_4.5H_2O$ into 60 ml of deionized water) containing manganese sulfate corresponding to equimolecular amounts as aluminum in the zeolite in an amount of 2.6 millimole, and the solution was agitated at the temperature of 40° C. for two hours. The $SiO_2/Al_2O_3$ ratio measured with fluorescent X-ray analysis about the proton type ZSM-5 zeolite was 50, its surface area was 380 m²/g, and its particle diameter was 150 µm or smaller. The resultant slurry was agitated under reduced pressure at the temperature of from 40 to 60° C. and moisture was evaporated spending about 2 hours, thereby obtained white powders. After drying the resultant powders in the air at the temperature of 120° C. for 8 hours, they were heated up to the temperature of 600° C. in muffle furnace by spending 4 hours, and further, they were baked at the temperature of 600° C. for 5 hours. Then, the baked powders were crushed, further, impregnated in an aqueous solution containing 0.4 g of lanthanum (prepared by dissolving 0.99 g of acetic acid lanthanum 1.5 hydrate into 60 ml of deionized water), thereby dried and baked in the same manner as supporting manganese, and finally obtained grayish white solids. The grayish white solids were further crushed among mortar and the resultant powders were passed through a sieve of 150 µm, and the sieved powders were named as La—Mn/HZSM-5 catalyst. The content of La and Mn each expressed as atomic ratio to aluminum among zeolite were 1.1 and 1.0 respectively.

Subsequently, a catalytic activity after processing high temperature steam treatment about the prepared catalyst was evaluated by means of pulse decomposition reaction of n-hexane.

Namely, the La—Mn/HZSM-5 catalyst prepared in Example 1 was compressed, crushed, sieved and molded to granular catalyst with about 1 mmΦ. This catalyst in an amount of 1 g was filled into fixed bed tubular reactor, and processed high temperature steam treatment (steam partial pressure: 40 kPa) by passing nitrogen and steam for 24 hours at the temperature of 700° C. After the termination of high temperature steam treatment, inside the reactor was purged with nitrogen, and setting the temperature of catalyst floor at 500° C., a pulse decomposition reaction of n-hexane was carried out. Passing nitrogen as carrier gas with a flow rate of 75 cm³/min, a conversion ratio of n-hexane at outlet was measured by applying a pulse of n-hexane (introduction fluid volume: 1 µl) into the reactor.

The results are shown in Table 1. Additionally, a result of evaluation after similarly processing unmodified HZSM-5 is also shown in Table 1 for reference.

Example 2

HZSM-5 catalyst modified with lanthanum and zirconium (La—Zr/HZSM-5 catalyst) was prepared in a similar manner as Example 1 except that the aqueous solution containing manganese sulfate was replaced by an aqueous solution dissolving oxyzirconyl nitrate (prepared by dissolving 0.69 g of $ZrO(NO_3)_2 \cdot 2H_2O$ into 60 ml of deionized water) in an amount of 2.6 millimole. The content of La and Zr each expressed as atomic ratio to aluminum among zeolite were 1.1 and 1.0 respectively.

The result of pulse decomposition reaction of n-hexane after high temperature steam treatment about this catalyst is shown in Table 1.

Example 3

A catalyst modified with lanthanum, manganese and zirconium (La—Mn—Zr/HZSM-5 catalyst) was prepared in a similar manner as Example 1 except that the aqueous solution containing manganese sulfate was replaced by an aqueous solution dissolving 1.95 millimole of manganese sulfate and 0.65 millimole of oxyzirconyl nitrate (prepared by dissolving 0.47 g of $MnSO_4 \cdot 5H_2O$ and 0.174 g of $ZrO(NO_3)_2 \cdot 2H_2O$ into 60 ml of deionized water). The content of La and (Mn+Zr) each expressed as atomic ratio to aluminum among zeolite were 1.1 and 1.0 (Mn+Zr) respectively.

The result of pulse decomposition reaction of n-hexane after high temperature steam treatment about this catalyst is shown in Table 1.

Example 4

The powder catalyst (La—Mn/HZSM-5 catalyst) prepared in Example 1 in an amount of 4 g was impregnated in diammonium hydrogenphosphate aqueous solution (prepared by dissolving 0.68 g of diammonium hydrogenphosphate into 60 ml of deionized water), and the resultant solution was agitated at the temperature of 40° C. for 2 hours. The resultant slurry was agitated under reduced pressure at the temperature of from 40 to 60° C. and moisture was evaporated spending about 2 hours, thereby obtained grayish white powders. After drying the resultant powders in the air at the temperature of 120° C. for 8 hours, they were heated up to the temperature of 600° C. in muffle furnace by spending 4 hours, and further, they were baked at the temperature of 600° C. for 5 hours. The grayish white powders were further crushed with mortar and the resultant powders were passed through a sieve of 150 µm, and the sieved powders were named as P—La—Mn/HZSM-5 catalyst. The content of La, Mn and P each expressed as atomic ratio to aluminum among zeolite were 1.1, 1.0 and 1.1 respectively.

The result of pulse decomposition reaction of n-hexane after high temperature steam treatment about this catalyst is shown in Table 1.

Example 5

The P—La—Zr/HZSM-5 catalyst was prepared in a similar manner as Example 4 except that the La—Mn/HZSM-5 catalyst was replaced by the La—Zr/HZSM-5 catalyst prepared in Example 2. The content of La, Zr and P each expressed as atomic ratio to aluminum among zeolite were 1.1, 1.0 and 1.1 respectively.

The result of pulse decomposition reaction of n-hexane after high temperature steam treatment about this catalyst is shown in Table 1.

Comparative Example 1

The powdery proton type ZSM-5 zeolite ($SiO_2/Al_2O_3$ ratio: 50) employed in Example 1 in an amount of 4 g was impregnated into an aqueous solution containing 0.4 g of lanthanum (prepared by dissolving 0.99 g of acetic acid lanthanum 1.5 hydrate into 60 ml of deionized water), and the resultant solution was agitated for 2 hours at the temperature of 40° C. The resultant slurry was agitated under reduced pressure at the temperature of from 40 to 60° C. and moisture was evaporated spending about 2 hours, thereby obtained white powders. After drying the resultant powders in the air at the temperature of 120° C. for 8 hours, they were heated up to the temperature of 600° C. in muffle furnace by spending 4 hours, and further, they were baked at the temperature of 600° C. for 5 hours. The white solids were further crushed with mortar and the resultant powders were passed through a sieve of 150 µm, and the sieved powders were named as La/HZSM-5 catalyst. The content of La expressed as atomic ratio to aluminum among zeolite was 1.1.

The result of pulse decomposition reaction of n-hexane after high temperature steam treatment about this catalyst is shown in Table 2.

Comparative Example 2

P—La/HZSM-5 catalyst supporting phosphor was prepared similarly as Example 4 except that 4 g of La/HZSM-5 catalyst obtained in Comparative Example 1 was employed. The content of La and P expressed as atomic ratio to aluminum among zeolite were equally 1.1.

The result of pulse decomposition reaction of n-hexane after high temperature steam treatment about this catalyst is shown in Table 2.

Comparative Example 3

The powdery proton type ZSM-5 zeolite ($SiO_2/Al_2O_3$ ratio: 50) employed in Example 1 in an amount of 4 g was impregnated into an aqueous solution (prepared by dissolving 0.62 g of $MnSO_4 \cdot 5H_2O$ into 60 ml of deionized water) containing manganese sulfate corresponding to equimolecular amounts as aluminum in the zeolite in an amount of 2.6 millimole, and the solution was agitated for 2 hours at the temperature of 40° C. The resultant slurry was agitated under reduced pressure at the temperature of from 40 to 60° C. and moisture was evaporated spending about 2 hours, thereby obtained white powders. After drying the resultant powders in the air at the temperature of 120° C. for 8 hours, they were heated up to the temperature of 600° C. in muffle furnace by spending 4 hours, and further, they were baked at the temperature of 600° C. for 5 hours. The solids were further crushed with mortar and the resultant powders were passed through a sieve of 150 μm, and the sieved powders were named as Mn/HZSM-5 catalyst. The content of Mn expressed as atomic ratio to aluminum among zeolite was 1.0.

The result of pulse decomposition reaction of n-hexane after high temperature steam treatment about this catalyst is shown in Table 2.

Comparative Example 4

HZSM-5 catalyst modified with zirconium (Zr/HZSM-5 catalyst) was prepared in a similar manner as Comparative Example 3 except that the aqueous solution containing manganese sulfate was replaced by an aqueous solution dissolving oxyzirconyl nitrate (prepared by dissolving 0.69 g of $ZrO(NO_3)_2 \cdot 2H_2O$ into 60 ml of deionized water) in an amount of 2.6 millimole. The content of Zr expressed as atomic ratio to aluminum among zeolite was each 1.0.

The result of pulse decomposition reaction of n-hexane after high temperature steam treatment about this catalyst is shown in Table 2.

Comparative Example 5

P—Mn/HZSM-5 catalyst supporting phosphor was prepared similarly as Example 4 except that 4 g of Mn/HZSM-5 catalyst obtained in Comparative Example 3 was employed. The content of Mn and P each expressed as atomic ratio to aluminum among zeolite were 1.0 and 1.1 respectively.

The result of pulse decomposition reaction of n-hexane after high temperature steam treatment about this catalyst is shown in Table 2.

TABLE 1

| Catalyst | | n-hexane conversion ratio (%) |
|---|---|---|
| Unmodified | HZSM-5 | 4.2 |
| Example 1 | La—Mn/HZSM-5 | 15.5 |
| Example 2 | La—Zr/HZSM-5 | 12.2 |
| Example 3 | La—Mn—Zr/HZSM-5 | 15.0 |
| Example 4 | P—La—Mn/HZSM-5 | 16.0 |
| Example 5 | P—La—Zr/HZSM-5 | 12.5 |

TABLE 2

| Catalyst | | n-hexane conversion ratio (%) |
|---|---|---|
| Comparative Example 1 | La/HZSM-5 | 4.5 |
| Comparative Example 2 | P—La/HZSM-5 | 5.2 |
| Comparative Example 3 | Mn/HZSM-5 | 6.5 |
| Comparative Example 4 | Zr/HZSM-5 | 5.5 |
| Comparative Example 5 | P—Mn/HZSM-5 | 6.8 |

As apparently shown by comparing Table 1 and Table 2, it is understood that the catalyst in Examples of the present invention maintains catalytic activity after high temperature steam treatment remarkably enhancing as compared with the unmodified catalyst or the catalyst in Comparative Examples.

Example 6

The La—Mn/HZSM-5 catalyst prepared in Example 1 was compressed, crushed, sieved and molded to granular catalyst with a diameters of about 1 mmΦ. This catalyst in an amount of 1 g was filled into a reaction tube with inside diameter of 10 mm and made of stainless steel (with interpolation pipe for thermocouple with outside diameter of 3 mm). The length of the catalytic layer was about 30 mm. Quartz sand was filled into the top and the bottom of the catalytic layer. While sending air with a flow rate of 40 cm³/min (at the temperature of 0° C., converted as 1 atmospheric pressure, the same hereunder) into the fixed bed reactor, the temperature of the catalytic layer was elevated up to 650° C. and the catalytic layer was preprocessed as it is for one hour. After the termination of the pretreatment, catalytic cracking reaction of n-butane was carried out under high temperature hydrothermal condition maintaining the temperature of the catalytic layer at 650° C., and feeding n-butane as material, nitrogen and steam each with the flow rate of 3.0 cm³/min, 30 cm³/min, and 0.5 g/h respectively.

The reaction product was analyzed by means of gas chromatography and the values of product yield and material conversion ratio were calculated respectively using the following equations:

Product yield (% by mass)=(mass of each component/mass of fed material)×100

Material conversion ratio (%)=(1−mass of unreacted material/mass of fed material)×100

The reaction results are shown in Table 3.

Example 7 and Example 8

The catalytic cracking reactions of n-butane were carried out in the same manner as Example 6 except that La—Zr/HZSM-5 prepared in Example 2, or P—La—Mn/HZSM-5 prepared in Example 4 was used as the catalyst in Example 7 and Example 8 respectively.

The reaction results are shown in Table 3.

Comparative Examples 6 and 7

The catalytic cracking reactions of n-butane were carried out in the same manner as Example 6 except that P—La/HZSM-5 prepared in Comparative Example 2, or Mn/HZSM-5 prepared in Comparative Example 3 was used as the catalyst in Comparative Example 6 and Comparative Example 7 respectively.

The reaction results are shown in Table 4.

In Tables 3 and 4, Y represents Product yield.

TABLE 3

|  |  | Example 6 | | Example 7 | | Example 8 | |
| --- | --- | --- | --- | --- | --- | --- | --- |
| Catalyst | | La—Mn/HZSM-5 | | La—Zr/HZSM-5 | | P—La—Mn/HZSM-5 | |
| Material | | n-butane | | n-butane | | n-butane | |
| Temperature (° C.) | | 650 | | 650 | | 650 | |
| Passing Time (hrs.) | | 2 | 50 | 2 | 50 | 2 | 50 |
| Material Conversion ratio (%) | | 94.9 | 91.5 | 96.3 | 92.7 | 93.8 | 90.2 |
| Y · wt % | Ethylene | 39.0 | 34.9 | 34.8 | 31.0 | 37.3 | 36.0 |
| | Propylene | 14.8 | 14.5 | 21.4 | 22.0 | 14.7 | 15.3 |
| | Butanes | 0.6 | 0.6 | 2.6 | 4.1 | 0.5 | 2.1 |
| | Aromatics | 5.2 | 6.2 | 2.8 | 2.7 | 4.0 | 2.4 |
| | Methane | 16.3 | 15.2 | 13.7 | 13.0 | 15.8 | 15.2 |
| | Ethane | 14.3 | 12.9 | 13.9 | 13.4 | 13.3 | 13.2 |
| | Propane | 1.0 | 2.2 | 1.2 | 1.3 | 1.1 | 1.1 |
| | Isobutane | 0.7 | 0.9 | 0.3 | 0.3 | 1.0 | 1.3 |
| | $C_{5+}$, Coke | 2.2 | 2.1 | 2.8 | 1.3 | 2.0 | 2.1 |
| | CO | 0.6 | 2.1 | 1.2 | 1.1 | 4.2 | 1.6 |
| | CO2 | 0 | 0.9 | 0.3 | 0.3 | 4.3 | 0.8 |

TABLE 4

|  |  | Comparative Example 6 | | Comparative Example 7 | |
| --- | --- | --- | --- | --- | --- |
| Catalyst | | P—La/HZSM-5 | | Mn/HZSM-5 | |
| Material | | n-butane | | n-butane | |
| Temperature (° C.) | | 650 | | 650 | |
| Passing Time (hrs) | | 2 | 50 | 2 | 50 |
| Material Conversion Ratio (%) | | 96.0 | 64.6 | 80.4 | 54.6 |
| Y · wt % | Ethylene | 38.9 | 22.2 | 23.2 | 17.7 |
| | Propylene | 18.3 | 15.8 | 16.6 | 12.4 |
| | Butanes | 2.2 | 3.2 | 1.7 | 2.4 |
| | Aromatics | 2.5 | 0 | 0.7 | 0 |
| | Methane | 14.5 | 9.8 | 18.8 | 10.4 |
| | Ethane | 13.9 | 9.3 | 12.6 | 7.9 |
| | Propane | 1.1 | 1.4 | 1.0 | 0.4 |
| | Isobutane | 1.5 | 2.3 | 1.1 | 1.7 |
| | $C_{5+}$, Coke | 0.9 | 0.1 | 0.8 | 0.1 |
| | Co | 2.3 | 0.5 | 4.4 | 1.8 |
| | CO2 | 1.1 | 0 | 6.7 | 2.1 |

As apparently shown by comparing Table 3 and Table 4, it is understood that the use of the catalyst prepared in Comparative Example extravagantly degrades conversion ratio and olefin yield in the case of prolonging the distribution time, and deteriorates durability in long time operation. On the other hand, the use of the catalyst prepared in Examples of the present invention maintains the conversion ratio and olefin yield at high values for a long time.

INDUSTRIAL APPLICABILITY

In accordance with the present invention, light olefins such as ethylene, propylene and so on can be produced stably for a long term with high yield of 50% or greater employing gaseous or liquid hydrocarbon as material and suppressing by-product such as aromatic hydrocarbons or heavy substances. Further, production of olefin can be carried out with economically advantageous condition at the temperature of at least 100° C. lower than the conventional cracking method.

What is claimed is:

1. A process for producing olefin by catalytic cracking of hydrocarbon material characterized in employing a catalyst consisting of a penta-sil zeolite comprising one or more rare earth elements and at least one of manganese and zirconium.

2. The process for producing olefin according to claim 1, wherein the content of said one or more rare earth elements in said catalyst falls within the range of from 0.4 to 20 expressed as atomic ratio of aluminum in zeolite.

3. The process for producing olefin according to claim 1, wherein the total content of manganese and zirconium in said catalyst falls within the range of from 0.1 to 20 expressed as mole ratio of aluminum in zeolite.

4. The process for producing olefin according to claim 1, wherein said catalyst further comprises phosphorous in an amount of from 0.1 to 5% by mole.

5. The process for producing olefin according to claim 1, wherein the mole ratio of $SiO_2/Al_2O_3$ among zeolite in said catalyst is from 25 to 800.

6. The process for producing olefin according to claim 1, wherein a catalytic reaction is carried out under the presence of steam.

7. The process for producing olefin according to claim 1, wherein the one or more rare earth elements is selected from the group consisting of La, Ce, Pr, Nd, Sm and Eu.

8. The process for producing olefin according to claim 2, wherein the content of said one or more rare earth elements in said catalyst falls within the range of from 0.6 to 5 expressed as atomic ratio of aluminum in zeolite.

9. The process for producing olefin according to claim 8, wherein the content of said one or more rare earth elements in said catalyst falls within the range of from 1 to 3 expressed as atomic ratio of aluminum in zeolite.

10. The process for producing olefin according to claim 3, wherein the total content of manganese and zirconium in said catalyst falls within the range of from 0.5 to 10 expressed as mole ratio of aluminum in zeolite.

11. The process for producing olefin according to claim 10, wherein the total content of manganese and zirconium in said catalyst falls within the range of from 1 to 5 expressed as mole ratio of aluminum in zeolite.

12. The process for producing olefin according to claim 7, wherein
the content of said one or more rare earth elements in said catalyst falls within the range of from 0.6 to 5 expressed as atomic ratio of aluminum in zeolite; and
the total content of manganese and zirconium in said catalyst falls within the range of from 0.5 to 10 expressed as mole ratio of aluminum in zeolite.

13. The process for producing olefin according to claim 12, wherein
the content of said one or more rare earth elements in said catalyst falls within the range of from 1 to 3 expressed as atomic ratio of aluminum in zeolite; and
the total content of manganese and zirconium in said catalyst falls within the range of from 1 to 5 expressed as mole ratio of aluminum in zeolite.

\* \* \* \* \*